United States Patent [19]

Cerf et al.

[11] Patent Number: 5,412,138

[45] Date of Patent: May 2, 1995

[54] PHOSPHORUS-CONTAINING ACRYLIC COMPOUNDS AND POLYMERS THEREOF

[75] Inventors: Martine Cerf, Metz; Jean-Luc Mieloszynski, Montigny Les Metz; Daniel Paquer, Vandoeuvre, all of France

[73] Assignee: Elf Atochem S.A., Paris-La Defense, France

[21] Appl. No.: 993,724

[22] Filed: Dec. 14, 1992

Related U.S. Application Data

[63] Continuation-in-part of Ser. No. 714,180, Jun. 14, 1991, abandoned.

[30] Foreign Application Priority Data

Jun. 14, 1990 [FR] France ............... 90 07438

[51] Int. Cl.$^6$ .................... C07F 9/113; C07F 9/173
[52] U.S. Cl. ........................................... 558/182
[58] Field of Search ................................. 558/182

[56] References Cited

U.S. PATENT DOCUMENTS

| | | | |
|---|---|---|---|
| 2,934,554 | 4/1960 | Lane | 558/182 X |
| 3,574,794 | 4/1971 | Hargis | 558/182 X |
| 4,581,180 | 4/1986 | Yokoshima et al. | 558/180 |
| 4,992,340 | 2/1991 | Dickie et al. | 427/44 |
| 5,055,497 | 10/1991 | Okada et al. | 523/116 |

OTHER PUBLICATIONS

Derwent Japanese Patents Report, vol. 6, No. 4, Jan. 26, 1967–Feb. 1, 1967.
Chem. Abstr. 104: 20387a (1986).
Chem. Abstr. 101: 238160f (1984).
Chem. Abstr. 98: 127292a (1983).
Chem. Abstr. 112: 240558n (1990).
Chem. Abstr. 109: 111754n (1988).
Chem. Abstr. 109: 170558z (1988).
Chem. Abstr. 109: 64145c (1987).

*Primary Examiner*—Mary C. Lee
*Assistant Examiner*—Michael G. Ambrose
*Attorney, Agent, or Firm*—Millen, White, Zelano, & Branigan

[57] ABSTRACT

These acrylic and methacrylic compounds are chosen from those of the formula:

$$H_2C=C(R^1)(C(=O)O-A-Y-P(OR)_2=X) \quad (I)$$

$$[H_2C=C(R^1)(C(=O)O-A-O)]_3 P=X \quad (II)$$

$$\left[[H_2C=C(R^1)(C(=O)O-A-O)]_2 P-S\right]_m Z \quad (III)$$

in which $R^1$ is H or $CH_3$; A is $(CH_2)_n$ or n is an integer from 2 to 12 or $-(CH_2CH_2O)_d-CH_2CH_2-$, d is an integer from 1 to 20; X is S or O; Y is S or O, under the condition that X is S and Y is O when A is $-(CH_2CH_2O)_d-CH_2CH_2-$; R is $C_1-C_{20}$alkyl or $-(CH_2)_pSR^3$ where p is an integer from 3 to 12 and $R^3$ is $C_1-C_{20}$-alkyl; m is an integer from 1 to 3; and Z is H, $R^2QH$, or $R^2$ is $C_2-C_{12}$-alkyl and Q is O or S, and the atoms of the metals from Groups IA, IIA, IIIA, IB, IIB, VIB, VIIB and VIII of the Periodic Table, on condition that Z is H or $R^2OH$ when m is 1 and m is the valence of Z when Z is a metal.

17 Claims, No Drawings

PHOSPHORUS-CONTAINING ACRYLIC COMPOUNDS AND POLYMERS THEREOF

CROSS-REFERENCE TO RELATED APPLICATION

This application is a continuation in part of application Ser. No. 07/714,180, filed Jun. 14, 1991, abandoned, entitled "PHOSPHORUS- AND SULFUR-CONTAINING ACRYLATES AND METHACRYLATES AND POLYMERS THEREOF" based on French Application 90 07439, Attorney Docket No. ATOCM 15.

BACKGROUND OF THE INVENTION

The present invention relates to new acrylates and methacrylates comprising at least one phosphorus atom and at least one other hetero atom, to a process for manufacturing them, to the preparation of new polymers and copolymers from said acrylates and methacrylates, and also to organic compounds comprising at least one phosphorus atom and at least one sulphur atom, which are useful intermediates in the synthesis of said acrylates and methacrylates.

The scientific and technical literature has already disclosed a large number of acrylic and methacrylic compounds carrying functions such as halogen, hydroxyl, thiol, epoxide, and the like. Each of these groups of compounds has already found various applications in different industries, due to the ease in polymerisation of the acrylic double bond. However, until now the scientific and technical literature has given few examples of acrylic and methacrylic compounds simultaneously carrying at least one phosphorus atom and at least one sulphur atom.

SUMMARY OF THE INVENTION

Accordingly, the present invention first relates to acrylic and methacrylic compounds chosen from those of the formula:

$$H_2C=C\begin{matrix}R^1\\\\C\\||\\O\end{matrix}O-A-Y-P(OR)_2 \quad \text{(I)}$$
$$\phantom{H_2C=C\begin{matrix}R^1\\\\C\\||\\O\end{matrix}O-A-Y-}||\phantom{(OR)_2}$$
$$\phantom{H_2C=C\begin{matrix}R^1\\\\C\\||\\O\end{matrix}O-A-Y-}X\phantom{(OR)_2}$$

in which:
R$^1$ is chosen from a hydrogen atom and a methyl radical,
A is chosen from $(CH_2)_n$ radicals for which n is an integer from 2 to 12 and a $-(CH_2CH_2O)_d-CH_2-CH_2-$ radical, where d is an integer ranging from 1 to 20,
X is chosen from sulphur and oxygen atoms,
Y is chosen from sulphur and oxygen atoms, on condition that X is a sulphur atom and Y is an oxygen atom when A is a $-(CH_2CH_2O)_d-CH_2CH_2-$ radical, and
R is chosen from alkyl radicals having 1 to 20 carbon atoms and $-(CH_2)_pSR^3$ groups in which p is an integer ranging from 3 to 12 and R$^3$ is an alkyl radical having 1 to 20 carbon atoms, with the provisos that:
(1) A does not represent $(CH_2)_n$, with n being an integer from 2 to 6 when each of Y and X represents an oxygen atom and R represents alkyl of 1-4 carbon atoms, and
(2) R$^1$ does not represent methyl when A is $(CH_2)_n$, with n being 2, and Y and X each represents a sulfur atom, and R represents ethyl.

It is also preferred with respect to proviso (1) that A does not represent an adjacent homolog of the compounds covered by proviso (1) and, still more preferably, A does not represent $(CH_2)_n$. In addition, it is even more preferred that aside from A not representing $(CH_2)_n$, with n being an integer from 2 to 6, it is preferred that Y or X represents S and/or R represents alkyl of at least 6 carbon atoms.

With respect to proviso (2), it is preferred that the compounds embraced by this proviso do not represent an adjacent homlog; for example, n us preferably an integer from 4 to 12. Even more preferred, A does not represent $(CH_2)_n$ under the circumstances of proviso (2) and even still more preferred is that aside from R$^1$ not representing methyl, Y or X represents oxygen and/or R represents alkyl of 4 to 20 carbon atoms;

those of the formula:

$$\left[H_2C=C\begin{matrix}R^1\\\\C\\||\\O\end{matrix}O-A-O\right]_3 P=X \quad \text{(II)}$$

in which:
R$^1$ is chosen from a hydrogen atom and a methyl radical,
A is chosen from $(CH_2)_n$ radicals for which n is an integer from 2 to 12 and a $-(CH_2CH_2O)_d-CH_2CH_2-$ radical, where d is an integer from 1 to 20, and
X is chosen from sulphur and oxygen atoms, with the proviso that A does not represent $-(CH_2)_n$, with n being an integer from 2 to 6 when X is oxygen. It is also preferred that adjacent homologs are also excluded, and even more preferred that n is an integer from 8 to 12 and/or X is sulfur;

and those of the formula:

$$\left[\left[H_2C=C\begin{matrix}R^1\\\\C\\||\\O\end{matrix}O-A-O\right]_2 P-S\right]_m Z \quad \text{(III)}$$
$$\phantom{xxxxxxxxxxxxxxxxxxxxxxxxxxxxx}||$$
$$\phantom{xxxxxxxxxxxxxxxxxxxxxxxxxxxxx}S$$

in which:
R$^1$ is chosen from a hydrogen atom and a methyl radical,
A is chosen from $(CH_2)_n$ radicals for which n is an integer from 2 to 12,
m is an integer ranging from 1 to 3, and
Z is chosen from a hydrogen atom, R$^2$QH radicals, R$^2$ being an alkyl radical having 2 to 12 carbon atoms and Q being chosen from oxygen and sulphur atoms, and atoms of the metals from Groups IA, IIA, IIIA, IB, IIB, VIB, VIIB and VIII of the Periodic Table, on condition that Z is chosen from a hydrogen atom and R²OH radicals when m is 1 and that m is the valence of Z when Z is a metal, with the proviso that R¹ does not represent methyl when A represents —(CH₂)ₙ, being 10, m is 1, and Z is a hydrogen atom. It is further preferred that adjacent homologs be excluded, and it is especially preferred that n is 2–7 or 12 and/or m is 2 or 3 and/or Z is other than a hydrogen atom.

The present invention also relates to a process for the preparation of acrylic and methacrylic compounds of formulae (I) to (III). Even though all these compounds have in common for their preparation the reaction of an acrylic or methacrylic compound of the formula:

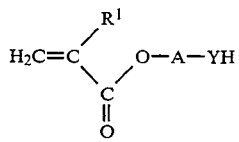 (IV)

in which R¹, A and Y have the same meanings as in formula (I) with a pentavalent compound of phosphorus, their synthesis nevertheless has characteristic features depending on whether compounds of the formula (I), of the formula (II) or of the formula (III) are prepared and of the latter, depending on the nature of Z. For this reason, the preparation process according to the invention will now be described with reference to each of the groups of compounds according to the invention.

The acrylic and methacrylic compounds of the formula (I) are prepared by reacting an acrylic or methacrylic compound of the formula (IV) as defined above, with a phosphorus-containing compound of the formula:

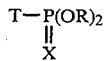 (V)

in which R and X have the same meanings as in formula (I) and T represents a halogen atom. The reaction is preferably carried out in the presence of a basic solvent which is capable of binding the hydrogen halide HT formed. Examples of such a solvent which may be mentioned are especially tertiary amines, including triethylamine, pyridine and dimethylaniline. The reaction is preferably carried out at a temperature between about 0° C. and 80° C. which, when a solvent is present, must not exceed the reflux temperature of said solvent. The duration of the reaction obviously depends on the nature of the compounds of formulae (IV) and (V) and the reaction temperature chosen. However, it is in general between about 1 and 20 hours. When the process according to the invention is carried out in this manner, a proportion of about 0.7 to 1.3 mol of the phosphorus-containing compound is generally used per 1 mol of acrylic or methacrylic compound of the formula (IV).

Although atmospheric pressure is in general satisfactory, the process according to the invention can likewise be carried out under reduced pressure, for example between about 0.05 and 1 bar.

Finally, the reaction according to the invention can be carried out in the presence of an effective amount of at least one polymerisation inhibitor. Examples of suitable polymerisation inhibitors which may be mentioned are especially phenothiazine, hydroquinone methyl ether, N,N-diethylhydroxylamine, nitrobenzene, di-tert.-butylcatechol, hydroquinone, p-anilinophenol, di(2-ethylhexyl)octylphenyl phosphite, 2,5-di-tert.-butyl-4-hydroxytoluene, methylene blue and mixtures thereof in any proportions. An efficient quantity of polymerisation inhibitor in general comprises between 0.05% and 0.5% by weight of acrylic or methacrylic compound.

At the conclusion of the reaction, it is possible to remove, if the case arises, the salt formed between the hydrogen halide and the basic solvent, for example by filtration. Isolation and purification of the acrylic or methacrylic compound of the formula (I) can be carried out by the well-known techniques of organic synthesis, especially washing with water in order to remove any excess hydroxylated (meth)acrylate of the formula (IV), column chromatography on silica gel for small amounts of the product or else distillation for large amounts.

Some of the phosphorus-containing compounds of the formula (V) are already well-known to one skilled in the art. They are especially those in which R is an alkyl radical, such as an ethyl radical or an isopropyl radical. This is not true of those in which R is a —(CH₂)ₚSR³ group in which p and R³ have the same meanings as in formula (I). The latter have been prepared here for the first time in order to serve especially as intermediates for the synthesis of acrylic and methacrylic compounds of the formula (I).

The phosphorus-containing compounds of the formula:

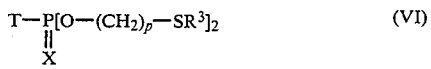 (VI)

in which T and X have the same meanings as in formula (IV) are prepared by reaction of a phosphorus oxyhalide or halogenosulphide of the formula PT₃X with an alcohol of the formula R³S(CH₂)ₚOH. The reaction is preferably carried out in the presence of a solvent or a solvent mixture at least lone of which is preferably a basic solvent capable of binding the hydrogen halide HT formed. Examples of basic solvents have been mentioned above. Examples of solvents miscible therewith which can be mentioned are benzene, toluene, the xylenes, dichloromethane, chloroform, diethyl ether, and the like. The reaction is preferably carried out at a temperature between about 10° C. and the reflux temperature, without, however, exceeding about 50° C. when X is a sulphur atom. The duration of the reaction, which is variable depending on the nature of the alcohol and the phosphorus oxyhalide or halogenosulphide, is in general between about 30 minutes and 4 hours. In general, the amount of alcohol is about 2 mol per 1 mol of phosphorus-containing compound. At the conclusion of the reaction, it is possible to remove, if the case arises, the salt formed between the hydrogen halide and the basic solvent, for example by filtration. The reaction generally produces, in the organic phase, a mixture of compounds of the formula:

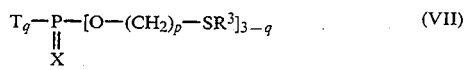 (VII)

in which T, X, p and R³ have the same meanings as in formulae (I) and (V) and q is an integer ranging from 0 to 2, in which mixture the major product is that in which q=1. These compounds can be separated by column chromatography. If the case arises, this mixture can be used directly for the preparation of the acrylic and methylacrylic compounds of the formula (I).

The acrylic and methacrylic compounds of the formula (II) are prepared by reacting an acrylic or methacrylic compound of the formula (IV) in which Y is oxygen with a compound of the formula $PXT_3$ in which X has the same meaning as in formula (II) and T represents a halogen atom. Examples of such compounds which may be mentioned are phosphorus oxychloride $POCl_3$ and phosphorus sulphochloride $PSCl_3$. The reaction is preferably carried out in the presence of a solvent or a mixture of solvents at least one of which is preferably a basic solvent capable of binding the hydrogen halide HT formed. Examples of basic solvents have been mentioned above. Examples of solvents miscible therewith which may be mentioned are benzene, toluene, the xylenes, dichloromethane, chloroform and diethyl ether. The reaction is preferably carried out at a temperature between about 50° C. and the reflux temperature of the solvent(s). The duration of the reaction, which is variable depending on the nature of the compound of the formula (IV), is in general between about 1 and 4 hours. To carry out the reaction, an amount of about 0.25 to 1.35 mol of compound $PXT_3$ is in general used per mole of the compound of the formula (IV).

Finally, the reaction according to the invention can be carried out in the presence of an effective amount of at least one polymerisation inhibitor. Examples of suitable polymerisation inhibitors which may be mentioned are especially phenothiazine, hydroquinone methyl ether, N,N-diethylhydroxylamine, nitrobenzene, di-tert.-butylcatechol, hydroquinone, p-anilinophenol, di(2-ethylhexyl)octylphenyl phosphite, 2,5-di-tert.-butyl-4-hydroxytoluene, methylene blue and mixtures thereof in any proportions. An efficient quantity of polymerisation inhibitor generally comprises between 0.05% and 0.5% by weight of acrylic or methacrylic compound.

At the conclusion of the reaction, the acrylic or methacrylic compound of the formula (II) is isolated and purified by filtration on silica gel or else by column chromatography.

The acrylic and methacrylic compounds of the formula (III) in which m is 1 and Z is a hydrogen atom are prepared by reacting an acrylic or methacrylic compound of the formula (IV) with phosphorus pentasulphide $P_2S_5$. The reaction is preferably carried out in the presence of a solvent such as benzene, toluene, xylenes, chloroform. The reaction is preferably carried out at a temperature between about 40° C. and the reflux temperature of the solvent. The duration of the reaction, which is variable depending on the nature of the compound of the formula (IV), is in general between about 15 minutes and 5 hours. In order to carryout the reaction, an amount of about 0.2 to 0.3 mol of phosphorus pentasulphide is in general used per mole of the compound of the formula (IV). At the conclusion of the reaction, the acrylic or methacrylic compound of the formula (III) is isolated by treating it with an alkaline solution (for example sodium hydroxide), washing with an organic solvent and regeneration by neutralisation with a dilute mineral acid (HCl, $H_2SO_4$).

The acrylic and methacrylic compounds of the formula (III) in which m is 1 and Z is an $R^2QH$ radical are prepared by first reacting an acrylic or methacrylic compound of the formula (III) in which m is 1 and Z is a hydrogen atom and which are obtained, for example, such as described above, with an alkylene oxide or sulphide (depending on whether Q is O or Q is S) of the general formula:

in which $R^4$ is chosen from a hydrogen atom and linear or branched alkyl radicals having 1 to 10 carbon atoms. Although this is not necessary, the reaction can be carried out in the presence of a solvent or a mixture of solvents such as those mentioned above. The reaction is preferably carried out at a temperature between about −10° C. and +40° C. and by using in general an amount of about 1 to 1.5 mol of alkylene oxide or sulphide for 1 mol of starting acrylic or methacrylic compound (III). Most frequently, the reaction leads to the formation of a mixture of two isomers in which the position of the hydroxyl or thiol function varies depending on the side on which the opening of the oxirane or thiirane ring takes place. At the conclusion of the reaction, the mixture of isomers is isolated directly, except in the case where a solvent is used, which is then evaporated off.

The acrylic and methacrylic compounds of the formula (III) in which m is the valence of Z and Z is the atom of a metal from Groups IA, IIA, IIIA, IB, IIB, VIB. VIIB and VIII of the Periodic Table are prepared by reacting an acrylic or methacrylic compound of the formula (III) in which m is 1 and Z is a hydrogen atom, obtained, for example, such as described above, with an inorganic salt of the metal Z in aqueous alkaline medium. Examples of metals Z which may be mentioned are alkali metals, such as sodium, potassium and lithium, alkaline earth metals, such as magnesium and calcium, and aluminium, zinc, cadmium, nickel, cobalt, iron and copper. The alkaline medium chosen for the reaction can be sodium hydroxide, potassium carbonate or generally any strong inorganic base. Examples of inorganic salts of the metal Z which may be mentioned are halides, oxides and sulphates. The reaction is preferably carried out at a temperature between about 20° C. and 60° C. and by using in general an amount of about 1 to 3 mol of acrylic or methacrylic compound for 1 mol of inorganic salt of the metal Z depending on the valence of the metal Z. At the conclusion of the reaction, the duration of which is in general between about 15 and 150 minutes, the acrylic or methacrylic metal compound of the formula (III) is extracted from the aqueous solution by means of an organic solvent, such as dichloromethane, chloroform, and the like.

Finally, the present invention also relates to the application of the new acrylic and methacrylic compounds described above to the synthesis of new polymers and copolymers. More precisely, the present invention relates to polymers and copolymers comprising at least one unit derived from at least one acrylic or methacrylic compound of the formula (I), formula (II) or the formula (III). Such (co)polymers may furthermore comprise at least one unit derived from at least one copolymerisable comonomer with said acrylic or methacrylic compound of the formula (I), formula (II) or formula (III), such as, for example:

an alkyl acrylate or methacrylate whose linear or branched alkyl group which is unsubstituted or substituted, for example, by at least one halogen atom, such as chlorine or fluorine and/or by at least one hydroxyl group, has 1 to 20 carbon atoms, an aryl acrylate or methacrylate, such as benzyl methacrylate, a vinylaromatic hydrocarbon, such as styrene, vinyltoluene, alpha-methylstyrene, 4-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 3-tert.-butylstyrene, 2,4-dichlorostyrene, 2,6-dichlorostyrene and 1-vinylnaphthalene, an unsaturated nitrile, such as acrylonitrile or methacrylonitrile, an N-substituted maleimide, such as N-ethylmaleimide, N-isopropylmaleimide, N-n-butylmaleimide, N-isobutylmaleimide, N-tert-butylmaleimide, N-n-octylmaleimide, N-cyclohexylmaleimide, N-benzylmaleimide and N-phenylmaleimide, an anhydride of an unsaturated dicarboxylic acid, such as maleic anhydride, itaconic anhydride, citraconic anhydride or tetrahydrophthalic anhydride, acrylic or methacrylic acid, an acrylate or methacrylate of a polyol, such as diacrylates and dimethacrylates of ethylene glycol, propylene glycol, 1,3-butanediol, 1,4-butanediol, 1,6-hexanediol, neopentyl glycol, 1,4-cyclohexanediol, 1,4-cyclohexanedimethanol, 2,2,4-trimethyl-1,3-pentanediol, 2-ethyl-2-methyl-1,3-propanediol, 2,2-diethyl-1,3-propanediol, diethylene glycol, dipropylene glycol, triethylene glycol, tripropylene glycol, tetraethylene glycol, tetrapropylene glycol, trimethylolethane, trimethylolpropane, glycerol, pentaerythritol, triacrylates and trimethacrylates of trimethylolethane, trimethylolpropane, glycerol, pentaerythritol, tetraacrylates and tetramethacrylates of pentaerythritol, di(meth)acrylates to hexa(meth)acrylates of dipentaerythritol, poly(meth)acrylates of mono- or polyethoxylated or mono- or polypropoxylated polyols, such as the triacrylate and trimethacrylate of triethoxylated trimethylolpropane and tripropoxylated trimethylolpropane; the triacrylate and trimethacrylate of tripropoxylated glycerol; the triacrylate, trimethacrylate, tetraacrylate and tetramethacrylate of tetraethoxylated pentaerythritol, an epoxidised acrylate or methacrylate chosen from 2-epoxyethylbicyclo[2.2.1]hept-5(6)-yl (meth)acrylate, epoxydicyclopentyloxyethyl acrylate and those of the formula:

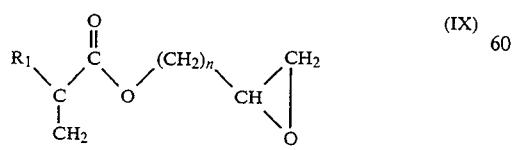

(IX)

in which R₁ is chosen from a hydrogen atom and a methyl radical and n is an integer ranging from 1 to 16, those of the formula:

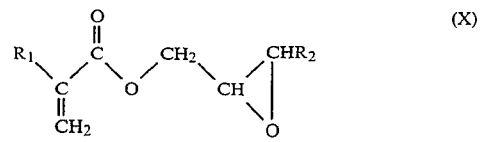

(X)

in which R₁ is chosen from a hydrogen atom and a methyl radical and R₂ is chosen from alkyl radicals having 1 to 12 carbon atoms and aryl radicals having 6 to 12 carbon atoms, and those of the formulae:

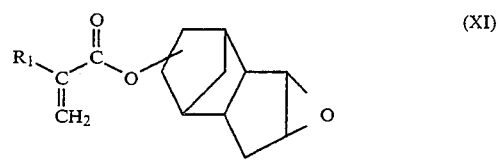

(XI)

and

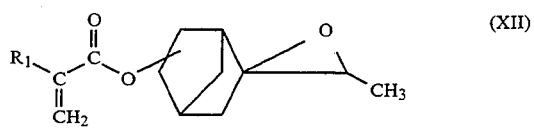

(XII)

in which R₁ is chosen from a hydrogen atom and a methyl radical, an acrylamide or methacrylamide, dialkylaminoalkyl acrylate or methacrylate and quaternary salts thereof, 2-(2-norbornyloxy) ethyl acrylate and methacrylate and 2-(dimethanodecahydro-2-naphthyloxy) ethyl acrylate and methacrylate, and acrylic and methacrylic oxazolidones chosen from those of the formula:

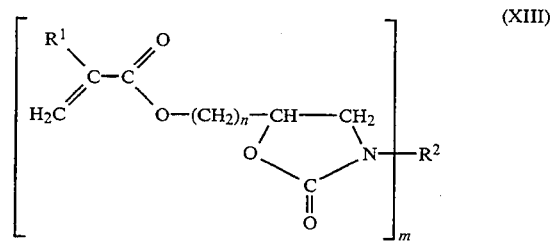

(XIII)

and those of the formula:

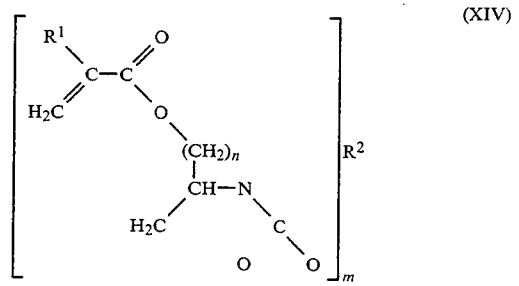

(XIV)

in which formulae:
R¹ is chosen from a hydrogen atom and a methyl radical,
n is an integer ranging from 1 to 12,
m is an integer ranging from 1 to 3, and $R^2$ is a linear, branched or cyclic alkyl or aromatic hydrocarbon radical having 5 to 12 carbon atoms, it being possible for said oxazolidones to be obtained by reaction of a compound carrying a (meth)acrylic function with a compound carrying at least one isocyanate function between 30° C. and 90° C.

Polymers and copolymers of this type are obtained by (co)polymerising at least one acrylic or methacrylic compound of the formula (I), formula (II) or formula (III) and, if desired, at least one copolymerisable comonomer, such as defined above, in the presence of at least one initiator of free radicals, such as a peroxide, a hydroperoxide or a diazo compound. The (co)polymerisation is in general carried out at a temperature between about 50° C. and 120° C. and by using one of the monomers as solvent. It can likewise be carried out in an emulsion in water, at a temperature between about 50° C. and 100° C. in the presence of at least one surface-active agent.

The polymers of this invention can be used in the same conventional manner as other acrylic and methacrylic polymers, e.g., formed into molded, cast, and extruded articles, coating materials, etc.

(In the above description and throughout the specification and claims, the numerical range of "from x to y", x and y being integers, is intended to include both x and y.)

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited above and below, and of corresponding French Application 90 07438, filed Jun. 14, 1990, are hereby incorporated by reference.

EXAMPLES 1 TO 4

0.1 mol of $PXCl_3$ (X=O, S) diluted in 30 ml of benzene are introduced into a three-neck flask equipped with a condenser, a thermometer, a dropping funnel and magnetic stirring.

0.2 mol of the sulphur-containing alcohol of the formula $(CH_3)_3C-S-(CH_2)_p-OH$ diluted in 10 ml of benzene and 0.2 mol of pyridine are added dropwise at 5° C.

At the end of the addition, the mixture is allowed to reach ambient temperature and is then heated [at reflux if X=O; at 50° C. if X=S] for 1 hour.

The pyridinium salt is removed by filtration, and the filtrate is washed with icewater.

The organic phase is dried over sodium sulphate and then concentrated.

The major product obtained of the formula

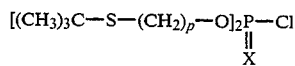

was characterised by proton nuclear magnetic resonance (NMR) by means of a JEOL PMX 60 SI spectrometer.

All the spectra obtained show chemical shifts at 1.3 ppm (s, 18H). In addition, they show chemical shifts, (expressed in ppm) which vary from product to product and whose characteristic features are shown in Table I below. This table summarises, as a function of the value of p and the meaning of X, the yield Y of the reaction (expressed in percent relative to the sulphur-containing alcohol) on the one hand and the data of the NMR spectrum on the other.

TABLE I

| | | | | $^1$H NMR | | |
|---|---|---|---|---|---|---|
| Ex. | p | X | Y | δ(CH$_2$O) | δ(CH$_2$S) | δ(CH$_2$) |
| 1 | 3 | S | 70 | 4.3 (m, 4H) | 2.6 (m, 4H) | 2.0 (m, 4H) |
| 2 | 3 | O | 70 | 4.3 (m, 4H) | 2.6 (m, 4H) | 2.0 (m, 4H) |
| 3 | 6 | S | 65 | 4.2 (m, 4H) | 2.5 (m, 4H) | 1.3 to 2.1 (m, 16H) |
| 4 | 6 | O | 75 | 4.2 (m, 4H) | 2.5 (m, 4H) | 1.3 to 2.1 (m, 16H) |

Moreover, the product from Example 2 was characterised by 31-phosphorus nuclear magnetic resonance with 5 proton decoupling, their standard being phosphoric acid. The spectrum which was obtained on a BRUCKER 80 MHz spectrometer shows a chemical shift at 4.6 ppm.

EXAMPLES 5 TO 13

10 mmol of hydroxyalkyl (meth)acrylate and 10 mmol of pyridine are introduced into a reactor equipped with a condenser, a thermometer, a dropping funnel and magnetic stirring. 10 mmol of chloride (RO)$_2$P(X)Cl are added dropwise at 15° C. The mixture is allowed to reach ambient temperature, and stirring is continued for 18 hours. 10 ml of anhydrous ether is then added to the reaction mixture, and the pyridinium salt is then removed. Removal of the ether on a rotary evaporator gives a colourless liquid.

The isolated product is then purified by washing with water, in order to remove any excess hydroxyalkyl (meth)acrylate, and/or by column chromatography on silica. The yield of (thio)phosphorylalkyl (meth)acrylate, expressed relative to phosphoryl chloride, is at least equal to 95% in each case.

The hydroxyalkyl methacrylate used for this synthesis has the formula (IV) with the following meanings, respectively:

—A=—(CH$_2$)$_2$—, (Examples 5 to 11)

—A=—CH$_2$)$_3$— (Examples 12 and 13)

The phosphoryl chloride used for this synthesis has the formula (V), the meanings of R and X being listed in Table II below. The (thio)phosphorylalkyl (meth)acrylates obtained were characterised by proton nuclear magnetic resonance by means of a JEOL PMX 60 SI spectrometer. All spectra obtained showed chemical shifts at 6.1 ppm (m, 1H), 5.6 ppm (m, 1H), 2.0 ppm (m, 3H) and, when R is a sulphur-containing radical (Examples 9 to 13), at 2.6 ppm (m, 4H). Moreover, they show chemical shifts (expressed in ppm) which vary from product to product and whose characteristic values are listed in Table II.

TABLE II

| Ex. | X | R | ¹H NMR δ(CH₂O) | δ(CH₂S) | δ(CH₂) |
|---|---|---|---|---|---|
| 5 | O | $C_2H_5$ | 4.0 to 4.4 (m, 8H) | | 1.3 (t, 6H) |
| 6 | S | $C_2H_5$ | 4.0 to 4.4 (m, 8H) | | 1.3 (t, 6H) |
| 7 | O | $CH(CH_3)_2$ | 4.3 (m, 4H)<br>4.6 (m, 2H) | | 1.3 (d, 12H) |
| 8 | S | $CH(CH_3)_2$ | 4.3 (m, 4H)<br>4.6 (m, 2H) | | 1.3 (d, 12H) |
| 9 | S | $(CH_2)_3SC(CH_3)_3$ | 4.0 to 4.4 (m, 8H) | 2.0 (m, 4H) | 1.3 (s, 18H) |
| 10 | O | $(CH_2)_6SC(CH_3)_3$ | 4.0 to 4.4 (m, 8H) | 1.3 to 2.1 (m, 16H) | 1.3 (s, 18H) |
| 11 | S | $(CH_2)_6SC(CH_3)_3$ | 4.0 to 4.4 (m, 8H) | 1.3 to 2.1 (m, 16H) | 1.3 (s, 18H) |
| 12 | O | $(CH_2)_3SC(CH_3)_3$ | 4.0 to 4.4 (m, 8H) | 2.0 (m, 6H) | 1.3 (s, 18H) |
| 13 | S | $(CH_2)_3SC(CH_3)_3$ | 4.0 to 4.4 (m, 8H) | 2.0 (m, 6H) | 1.3 (s, 18H) |

EXAMPLES 14 AND 15

0.1 mol of phosphorus oxychloride $POCl_3$ diluted in 30 ml of benzene is introduced under a nitrogen atmosphere into a reactor equipped with a condenser, a thermometer, a dropping funnel and magnetic stirring. 0.35 mol of 2-hydroxyethyl acrylate (Example 14) or 2-hydroxyethyl methacrylate (Example 15), 0.35 mol of pyridine and 15 ml of benzene are added dropwise at 5° C. At the end of the addition, the mixture is heated at 60° C. for 2 hours. The pyridinium salt is removed by filtration, and the filtrate is washed with icewater. The organic phase is dried over sodium sulphate and then concentrated. This gives a yield of 45% (relative to phosphorus oxychloride) of yellowish oily liquids corresponding to the products of the formula (II) in which n is 2, X is oxygen and $R^1$ is hydrogen (Example 14) or a methyl radical (Example 15). These products were characterised by 31-phosphorus nuclear magnetic resonance under the same conditions as those of Example 4. The spectra obtained show a chemical shift at $-1.75$ ppm relative to phosphoric acid.

EXAMPLES 16 TO 18

0.12 mol of hydroxyalkyl methacrylate and 100 ml of benzene are introduced under a nitrogen atmosphere at a temperature of 20° C. into a reactor equipped with a condenser, a thermometer, a dropping funnel and magnetic stirring. The mixture is heated to reflux, and 0.03 mol of phosphorus pentasulphide $P_2S_5$ is then added. At the end of the addition, heating at 80° C. is continued until $P_2S_5$ has completely disappeared (30 minutes in the case of Examples 17 and 18, 2 hours in the case of Example 16). Evaporation of the solvent gives the compounds of the formula:

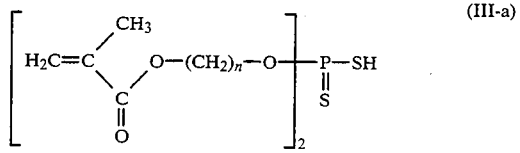
(III-a)

in the form of clear pale yellow liquids and a yield of 100%, relative to the hydroxyalkyl methacrylate.

The hydroxyalkyl methacrylates used are as follows:
2-hydroxyethyl methacrylate (n=2) in Example 16.
3-hydroxypropyl methacrylate (n=3) in Example 17.
6-hydroxyhexyl methacrylate (n=6) in Example 18.

The compounds of the formula (III-a) obtained were characterised by proton nuclear magnetic resonance by means of a JEOL PMX 60 SI spectrometer. All spectra obtained show chemical shifts at 6.1 ppm (m, 2H), 5.55 ppm (m, 2H), 2.0 ppm (m, 6H). Moreover, they show chemical shifts (expressed in ppm) which vary from product to product and whose values are shown in Table III.

TABLE III

| Example | n | δ(CH₂—O) | δ(CH₂) | δ(SH) |
|---|---|---|---|---|
| 18 | 2 | 4.3 (m, 8H) | | 3.0 (s, 1H) |
| 19 | 3 | 4.3 (m, 8H) | 1.4 to 2.1 (m, 4H) | 3.1 (s, 1H) |
| 20 | 6 | 4.2 (m, 8H) | 1.4 to 2.1 (m, 16H) | 3.0 (s, 1H) |

EXAMPLES 19 TO 21

0.2 mol of a compound obtained in one of Examples 16 to 18 and then 0.22 mol of aqueous sodium hydroxide solution (0.7N) are introduced into a reactor equipped with magnetic stirring, the mixture is then heated to 40° C., and 0.11 mol of zinc sulphate in aqueous solution is added and heating is continued for 1 hour. The mixture is extracted with dichloromethane, and the product is isolated by evaporation of the solvent. This gives the compounds of the formula:

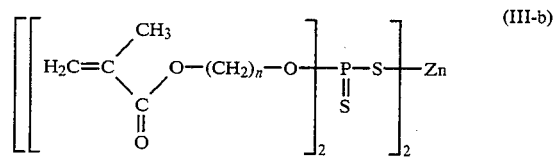
(III-b)

in the form of a thick yellow oil and the yield Y indicated in Table IV below.

These compounds were characterised by proton nuclear magnetic resonance by means of a JEOL PMX 60 SI spectrometer.

All spectra obtained show chemical shifts at 6.1 ppm (m, 4H), 5.6 ppm (m, 4H), 4.3 ppm (m, 16H) and 2.0 ppm (m, 12H). Moreover, they show a chemical shift expressed in ppm which varies from product to product and is listed in Table IV. These products were also characterised by 31-phosphorus nuclear magnetic resonance under the same conditions as those of Example 4. The chemical shifts (expressed in ppm) relative to $H_3PO_4$ are indicated in Table IV.

TABLE IV

| Example | n | Y | δ(CH₂) | ³¹P NMR |
|---|---|---|---|---|
| 19 | 2 | 95 | | 96.4 |
| 20 | 3 | 73 | 2.2 (m, 8H) | 96.0 |
| 21 | 6 | 90 | 1.3 to 2.3 (m, 32H) | 96.3 |

EXAMPLES 22 TO 24

0.1 mol of a compound obtained in one of Examples 18 to 20 and 0.11 mol of propylene oxide are introduced at 0° C. into a reactor equipped with a condenser, a thermometer, a dropping funnel and magnetic stirring, the temperature is then brought to 23° C., and the mixture is allowed to react for two hours. This gives the compounds of the formula:

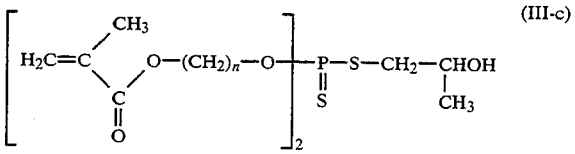

and

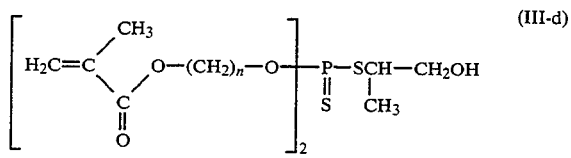

in a yield of 100% whose mixture was characterised by proton nuclear magnetic resonance by means of a JEOL PMX 60 SI spectrometer.

All spectra obtained show chemical shifts at 6.1 ppm (m, 2H), 5.6 ppm (m, 2H), 4.3 ppm (m, 9H), 2.7 ppm (s), 2.8 to 3.3 ppm (m, 2H), 2.0 ppm (m, 6H) and 1.3 ppm (d, 3H). Moreover, they show a chemical shift (expressed in ppm), which varies from product to product and is listed in Table V.

TABLE V

| Example | n | δ($CH_2$) | $^{31}P$ NMR (III-c) | (III-d) |
|---|---|---|---|---|
| 22 | 2 | | 97.4 | 96.4 |
| 23 | 3 | 2.1 (m, 4H) | 96.1 | 95.6 |
| 24 | 6 | 1.3 to 2.2 (m, 16H) | 95.8 | 95.4 |

These compounds were likewise characterised by 31-phosphorus nuclear magnetic resonance under the same conditions as those of Example 4. As determined by the spectra, the proportion of isomer (III-c) is 85% and that of isomer (III-d) 15%. The chemical shifts observed for each of the isomers and expressed in ppm are shown in Table V.

Polymers and copolymers can be made from any and all of the monomers produced in the above examples.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. Acrylic and methacrylic compounds chosen from those of the formula:

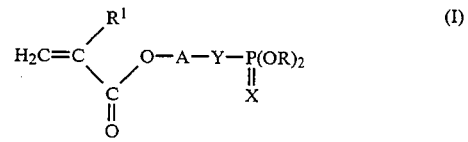

in which:
$R^1$ is chosen from a hydrogen atom and a methyl radical,
A is chosen from $(CH_2)_n$ radicals for which n is an integer from 2 to 12 and a —$(CH_2CH_2O)_d$—$CH_2$—$CH_2$— where d is an integer ranging from 1 to 20,
X is chosen from sulphur and oxygen atoms,
Y is chosen from sulphur and oxygen atoms, on condition that X is a sulphur atom and Y is an oxygen atom when A is a —$(CH_2CH_2O)_d$—$CH_2CH_2$— radical, and
R is chosen from alkyl radicals having 1 to 20 carbon atoms and —$(CH_2)_pSR^3$ group in which p is an integer ranging from 23 to 12 and $R^3$ is an alkyl radical having 1 to 20 carbon atoms,
with the proviso that A does not represent $(CH_2)_n$, when Y and X both represent an oxygen atom or both represent a sulfur atom and R represents alkyl of 1–20 carbon atoms,
those of the formula:

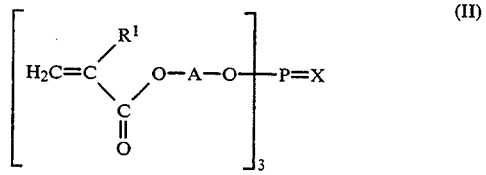

in which:
$R^1$ is chosen from a hydrogen atom and a methyl radical,
A is chosen from $(CH_2)_n$ radicals for which n is an integer from 2 to 12 and a —$(CH_2CH_2O)_d$—$CH_2CH_2$— radical, where d is an integer from 10 to 20, and
with the proviso that A does not represent —$(CH_2)_n$, when X is oxygen,
X is chosen from sulphur and oxygen atoms, and those of the formula

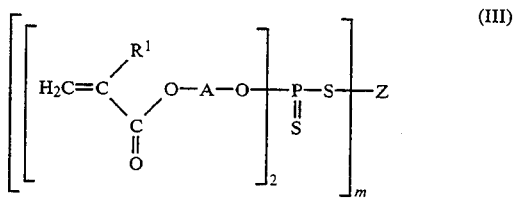

in which:
$R^1$ is chosen from a hydrogen atom and a methyl radical,
A is chosen from $(CH_2)_n$ radicals for which n is an integer from 2 to 12,
m is an integer ranging from 1 to 3, and
Z is chosen from a hydrogen atom, $R^2QH$ radicals, $R^2$ being an alkyl radical having 2 to 12 carbon atoms and Q being chosen from oxygen and sulphur atoms, and atoms of the metals from Groups IA, IIA, IIIA, IB, IIB, VIB, VIIB and VIII of the Periodic Table, on condition that Z is R²OH when m is 1 and that m is the valence of Z when Z is a metal.

2. A compound according to claim 1 of the formula (I).

3. Acrylic and methacrylic compounds chosen from those of the formula:

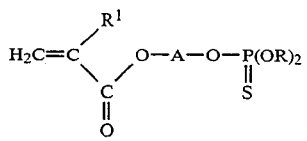

in which:

R¹ is chosen from a hydrogen atom and a methyl radical,

A is chosen from (CH₂)ₙ radicals for which n is an integer from 2 to 12 and a —(CH₂CH₂O)$_d$—CH₂—CH₂— radical, where d is an integer ranging from 1 to 20, and R is chosen from alkyl radicals having 1 to 20 carbon atoms and —(CH₂)$_p$SR³ groups in which p is an integer ranging from 3 to 12 and R³ is an alkyl radical having 1 to 20 carbon atoms.

4. A compound according to claim 3, wherein R is an alkyl radical having 1-20 carbon atoms.

5. A compound according to claim 4, wherein R is ethyl or isopropyl.

6. A compound according to claim 5, wherein R is ethyl.

7. A compound according to claim 6, wherein A is (CH₂)ₙ.

8. A compound according to claim 7, wherein n is 2.

9. A compound according to claim 8, wherein R¹ is methyl.

10. A compound according to claim 2, wherein n is an integer from 8 to 12.

11. A compound according to claim 2, wherein X or Y represents a sulfur atom.

12. A compound according to claim 10, wherein X or Y represents a sulfur atom.

13. A compound according to claim 12, wherein R represents alkyl of at least 6 carbon atoms.

14. Acrylic and methacrylic compounds chosen from those of the formula:

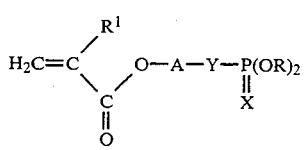

in which:

R¹ is chosen from a hydrogen atom and a methyl radical,

A is chosen from (CH₂)ₙ radicals for which n is an integer from 2 to 12 and a —(CH₂CH₂O)$_d$—CH₂—CH₂— radical, where d is an integer ranging from 1 to 20, X is chosen from sulphur and oxygen atoms, Y is chosen from sulphur and oxygen atoms, on the condition that X is a sulphur atom and Y is an oxygen atom when A is a —(CH₂CH₂O)$_d$—CH₂—CH₂— radical, and R is an —(CH₂)$_p$SR³ group in which p is an integer ranging from 3 to 12 and R³ is an alkyl radical having 1 to 20 carbon atoms.

15. An acrylic or methacrylic compound of the formula:

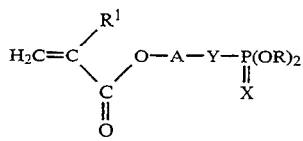

in which:

R¹ is a hydrogen atom or a methyl radical,

A is a (CH₂)ₙ radicals for which n is an integer from 2 to 12 or a —(CH₂CH₂O)$_d$—CH₂—CH₂— radical, where d is an integer ranging from 1 to 20, X is a sulphur or oxygen atom, Y is a sulphur or oxygen atom, R is an alkyl radicals having 1 to 20 carbon atoms or a —(CH₂)$_p$—SR³ group in which p is an integer ranging from 3 to 12 and R³ is an alkyl radical having 1 to 20 carbon atoms, with the provisos that:

X is a sulphur atom and Y is an oxygen atom when A is a —(CH₂CH₂O)$_d$—CH₂CH₂— radical, X is a sulfur atom when Y is an oxygen atom and R is alkyl A is not (CH₂)ₙ when both X and Y are S or both are O, and R is alkyl.

16. An acrylic or methacrylic compound of the formula:

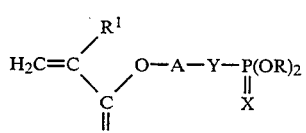

in which:

R¹ is a hydrogen atom or a methyl radical,

A is a (CH₂)ₙ radical for which n is an integer from 2 to 12 or a —(CH₂CH₂O)$_d$—CH₂—CH₂— radical, where d is an integer ranging from 1 to 20, X is a sulphur or oxygen atom, Y is a sulphur or oxygen atom, R is an alkyl radicals having 1 to 20 carbon atoms or a —(CH₂)$_p$SR³ group in which p is an integer ranging from 3 to 12 and R³ is an alkyl radical having 1 to 20 carbon atoms, with the proviso that:

X is a sulphur atom and Y is an oxygen atom when A is a —(CH₂CH₂O)$_d$—CH₂CH₂— radical, X is a sulfur atom when Y is an oxygen atom, A is not (CH₂)ₙ when both X and Y are S or both are O, and R is alkyl.

17. Acrylic and methacrylic compounds of the formula:

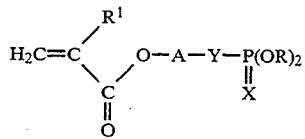

in which:

R¹ is a hydrogen atom or a methyl radical,

A is a $(CH_2)_n$ radical in which n is an integer from 2 to 12 or a $-(CH_2CH_2O)_d-CH_2-CH_2-$ radical, where d is an integer ranging from 1 to 20, X is sulphur or oxygen, Y is sulphur or oxygen, on condition that X is a sulphur atom and Y is an oxygen atom when A is a $-(CH_2CH_2O)_d-CH_2CH_2-$ radical, and R is an alkyl radical having 6 to 20 carbon atoms or a $-(CH_2)_pSR^3$ group in, which p is an integer ranging from 3 to 12 and $R^3$ is an alkyl radical having 1 to 20 carbon atoms, with the proviso that where R is alkyl, X or Y is sulfur.

* * * * *

UNITED STATES PATENT AND TRADEMARK OFFICE
CERTIFICATE OF CORRECTION

PATENT NO. : 5,412,138
DATED : May 2, 1995
INVENTOR(S) : Martine CERF et al.

It is certified that error appears in the above-indentified patent and that said Letters Patent is hereby corrected as shown below:

Claim 1, column 14, line 23:

After from delete " 2 ".

Signed and Sealed this

Third Day of October, 1995

Attest:

BRUCE LEHMAN

*Attesting Officer*  *Commissioner of Patents and Trademarks*